United States Patent [19]

Kyncl et al.

[11] Patent Number: 5,212,176
[45] Date of Patent: May 18, 1993

[54] R(+)-TERAZOSIN

[75] Inventors: John J. Kyncl, Lake Forest; Bruce W. Horrom, Waukegan, both of Ill.

[73] Assignee: Abbott Laboratories, Abbott Park, Ill.

[21] Appl. No.: 546,349

[22] Filed: Jun. 29, 1990

[51] Int. Cl.$^5$ .................. A61K 31/505; C07D 239/84
[52] U.S. Cl. ..................................... 514/254; 544/291
[58] Field of Search ....................... 514/254; 544/291

[56] References Cited

U.S. PATENT DOCUMENTS

| 4,026,894 | 5/1977 | Winn et al. | 544/291 |
| 4,112,097 | 9/1978 | Winn et al. | 514/260 |
| 4,251,532 | 2/1981 | Roteman | 514/254 |

OTHER PUBLICATIONS

"Advanced Organic Chemistry" by Jerry March (1985) John Wiley & Sons publishers pp. 82-87.
T. Nagatomo, et al., Chem. Pharm. Bull. 35(4)1629-1632 (1987).

Primary Examiner—Thurman K. Page
Assistant Examiner—Jyothsna Venkat
Attorney, Agent, or Firm—Jerry F. Janssen

[57] ABSTRACT

R(+)-2-[4-[(tetrahydro-2-furanyl)carbonyl]-1-piperazinyl]-6,7-dimethoxy-4-quinazolinamine hydrochloride or a pharmaceutically acceptable salt or hydratet hereof (terazosin), substantially free of the S(−)-enantiomer.

6 Claims, No Drawings

R(+)-TERAZOSIN

TECHNICAL FIELD

This invention relates to compounds having pharmacological activity, to pharmaceutical compositions containing such compounds and to medical methods of treatment. More particularly, this invention concerns R(+)-2-[(tetrahydro-2-furanyl)carbonyl]-1-piperazinyl]-6,7-dimethoxy-4-quinazolinamine, substantially free of the S(−)-enantiomer, its pharmaceutically acceptable salts and its hydrates, to pharmaceutical compositions containing the compound, and to medical methods of treatment employing the compound.

BACKGROUND OF THE INVENTION

The adrenergic nervous control of bodily functions is mediated by two hormones: norepinephrine, which is generated in the adrenergic nerves and released from their endings, and epinephrine, which is synthesized in the adrenal medulla and secreted into circulating blood. Both of these hormones act by binding to special receptors, designated as "adrenergic" receptors, which mediate the signal of the hormones to the intracellular biochemical mechanisms leading to stimulation of diverse physiological functions. Such functions include contraction of vascular smooth muscle (which can increase blood pressure), acceleration of heart rate, induction of metabolic changes in the liver, modulation of central nervous system activity, and many others.

The adrenergic receptors are proteins embedded in cellular membranes having unique, specific amino acid sequences. Four general families of adrenergic receptors have been identified and designated $\alpha_1$, $\alpha_2$, $\beta_1$ and $\beta_2$, all of which can be stimulated by norepinephrine and epinephrine. These receptor families, however, differ such that specific agents have been developed which can selectively stimulate or inhibit each type of receptor. The degree and type of receptor selectivity for a particular agonist or antagonist agent is an important pharmacological property of such an agent and can have substantial impact on its biological activity, side effects and safety. In general, excessive stimulation of the $\alpha_1$ adrenoreceptor is a hallmark of numerous pathological situations and disease states such as hypertension, congestive heart failure, cardiac hyperplasia, benign prostatic hyperplasia, hyperinsulinemia, lipid disorders, impotency, as well as many others.

Importantly, the $\alpha_2$ adrenoreceptors, which are very similar to the $\alpha_1$ species, regulate the release of the two adrenergic hormones, norepinephrine and epinephrine, and impact on the overall level of adrenergic activity. The stimulation of $\alpha_2$ receptors by an agonist inhibits the secretion of norepinephrine and epinephrine, whereas $\alpha_2$ antagonist activity increases the secretion of these hormones substantially. Thus, the $\alpha_1/\alpha_2$ adrenoreceptor selectivity of an $\alpha$-antagonist is very important and a desirable feature.

A number of non-selective $\alpha$-adrenergic blockers, such as phenoxybenzamine and phentolamine, have prominent effects on both $\alpha_1$ and $\alpha_2$ receptors. It is the $\alpha_2$ component of their adrenergic receptor activity which increases the adrenergic hormone secretion and thus limits their therapeutic use. Typical of such $\alpha_2$ antagonist effects are increases in plasma catecholamine levels, increases in heart rate and contractility, and other highly undesirable therapeutic phenomena.

It is therefore desirable to obtain $\alpha_1$ blocking agents which have greater $\alpha_1/\alpha_2$ selectivity than agents currently available. Such selectivity permits treatment of diseases characterized by elevated $\alpha_1$ adrenergic activity without stimulating $\alpha_2$ adrenoreceptor-mediated secretion of norepinephrine and epinephrine.

2-[4[(Tetrahydro-2-furanyl)carbonyl]-1-piperazinyl]-6,7-dimethoxy-4-quinazolinamine, also commonly known by its generic name, terazosin, has been known for several years as an antihypertensive drug. U.S. Pat. No. 4,026,894 discloses and claims the compound and U.S. Pat. No. 4,112,097 discloses and claims pharmaceutical compositions containing the compound and a method of treating hypertension in mammals. U.S. Pat. No. 4,251,532 discloses and claims the dihydrate of the hydrochloride salt of terazosin. The latter patent also discloses and claims pharmaceutical compositions comprising the hydrochloride dihydrate and a method of treating hypertension. While the terazosin molecule possesses a single chiral center, and can thus exist in two enantiomeric forms, none of these patents discusses this optical property of the molecule or mentions the two enantiomers.

In 1987, Nagatomo and coworkers reported the binding of the racemic compound and the individual enantiomers to $\alpha$-receptors in dog brain and aorta tissue (Nagatomo, et al., *Chem. Pharm. Bull.*, 35(4): 1629–1632 (1987)). Their data indicate that, while both enantiomers and the racemic compound bind selectively to the $\alpha_1$ receptors, little difference appeared to exist between the degrees of selectivity of the two enantiomers for $\alpha_1$ receptors over $\alpha_2$ receptors. This article did not report any data to indicate the optical purity of the materials employed.

SUMMARY OF THE INVENTION

It has now been found that the two enantiomeric forms of 2-[4-[(tetrahydro-2-furanyl)carbonyl]-1-piperazinyl]-6,7-dimethoxy-4-quinazolinamine (terazosin) can be resolved, and a significant difference exists in the degree of selective binding the the R(+)- and S(−)-enantiomers at the $\alpha$-adrenergic receptors, resulting in important unexpected pharmacological properties and in their toxicity. The lack of affinity of the R(+)-enantiomer of terazosin for the $\alpha_2$ receptors compared to that of either the S(−)-enantiomer or the racemic compound is believed to confer advantages on the R(+)-enantiomer as a pharmaceutical agent.

The present invention thus provides, in one embodiment, the compound R(+)-2-[4-[(tetrahydro-2-furanyl)carbonyl]-1-piperazinyl]-6,7-dimethoxy-4-quinazolinamine, its pharmaceutically acceptable salts and hydrates, substantially free of the S(−) enantiomer.

In another embodiment, there are provided pharmaceutical compositions comprising a therapeutically effective amount of R(+)-2-[4-[(tetrahydro-2-furanyl)carbonyl]-1-piperazinyl]-6,7-dimethoxy-4-quinazolinamine, a pharmaceutically acceptable salt and/or hydrate thereof, substantially free of the S(−)-enantiomer, in combination with a pharmaceutically acceptable carrier.

In a further embodiment of the present invention there is provided a method for treating disease states characterized by abnormally elevated levels of $\alpha_1$ adrenergic activity, particularly hypertension, congestive heart failure, hyperinsulinemia and benign prostatic hyperplasia, in a mammal in need of such treatment comprising administering a therapeutically effective amount of R(+)-2-[4-[(tetrahydro-2-furanyl)carbonyl]-1-piperazinyl]-6,7-dimethoxy-4-quinazolinamine or a pharmaceutically acceptable salt orhydrate thereof substantially free of the S(−)-enantiomer.

DETAILED DESCRIPTION

R(+)-2-[4-[(tetrahydro-2-furanyl)carbonyl]-1-piperazinyl]-6,7-dimethoxy-4-quinazolinamine or a pharmaceutically acceptable salt and/or hydrate thereof, substantially free of the S(−)-enantiomer has utility for the treatment or amelioration of disease states which are modulated by α-adrenergic receptor blocking agents. These disease states are recognized in the literature to include hypertension, congestive heart failure, cardiac arrhythmia, pulmonary hypertension, arterioconstriction, and benign prostatic hyperplasia (see, for example, W. H. Frishman and Shlomo Charlap, "Adrenergic Receptors as Pharmacological Targets: The Alpha Adrenergic Blocking Drugs," Chapter 4 in *Adrenergic Receptors in Man*, Paul A. Insel, Ed., Marcel Dekker, Inc., New York.

The term "pharmaceutically acceptable salts" refers to the relatively non-toxic, inorganic and organic acid addition salts of the compound of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactobionate, laurylsulphonate salts and the like. (See, for example S. M. Berge, et al., "Pharmaceutical Salts," *J.Pharm.Sci.*, 66: 1-19 (1977) which is incorporated herein by reference.) The particularly preferred salt of this invention is the hydrochloride.

In accordance with the present invention, the two enantiomers have now been resolved, and the optical rotations of the hydrochloride salt dihydrates have been found to be $[a]_D = +23.9°$ (C=1, H$_2$O) for the dextrorotatory enantiomer and $[a]_D = -23.1°$ (C=1, H$_2$O) for the levorotatory enantiomer.

Measurement of the $a_1$ and $a_2$ binding of the racemic compound and the resolved enantiomers shows a higher degree of selectivity for $a_1$ receptor for the dextrorotatory enantiomer, R(+)-2-[4-[(tetrahydro-2-furanyl)carbonyl]-1-piperazinyl]-6,7-dimethoxy-4-quinazolinamine hydrochloride as shown by the data appearing in Table 1.

Binding of a compound at $a_1$ and $a_2$ receptor sites is typically determined by allowing the test compound to compete with radiolabeled compounds which are known to selectively bind at each site. The technique is well known and described in the literature. The pK$_I$, or negative logarithm of the binding equilibrium constant, is determined from the experimental data for each receptor and the degree of selectivity of the compound in question for $a_1$ over $a_2$ receptors can be measured by the antilogarithm of the differences between the pK$_I$ values for the two receptors.

α-Adrenergic binding data were obtained for the two enantiomers of terazosin and the racemic compound. Tissue from the liver and cerebral cortex of male Sprague-Dawley rats was homogenized in ice-cold assay buffer (Tris-HCl, 50 mM, pH 7.0 and 22° C.).

After centrifugation at 48,000 g for ten minutes the resulting pellets, containing cellular membranes containing α-receptors, were resuspended in 20 volumes of assay buffer and recentrifuged for ten minutes at 48,000 g. Liver membranes were diluted 200-fold and cerebral cortex tissues 50-fold with assay buffer.

Binding to $a_1$ adrenergic receptors was characterized with liver membranes in competition studies using tritiated prazosin (82 Ci/mmol, DuPont NEN; 0.2 nM) and six concentrations of each test compound at half-log incremental concentrations. Binding to $a_2$ adrenergic receptors was characterized in cerebral cortex tissue using tritiated rauwolscine (82.2 Ci/mMol, DuPont NEN; 0.5 nM) and six concentrations of competing test compound. Equilibrium binding was characterized after a 50 minute incubation period at 22° C. Bound radioligand was separated from radioligand in solution by filtration under vacuum through Whatman 935 AH filters. After washing five times with ice-cold assay buffer, the filters were immersed in 3 ml of Ready-Solv EP Scintillation fluid (Beckman) and counted in a Beckman LS3801 counter for 10 minutes or to a preset counting error of 4.5% at 50% counting efficiency. The concentration at which 50% of the specifically bound radioligand was displaced by the test compound (IC$_{50}$) was calculated and converted to an equilibrium dissociation constant (K$_I$) using the formula:

$$K_I = IC_{50}/(1+[L]/K_D)$$

where [L] is the concentration of radioligand and K$_D$ is the equilibrium dissociation constant of the radioligand for the receptor. The mean pK$_I$ values for the R(+), S(−), and racemic terazosin appear in Table 1.

TABLE 1

α-Adrenergic Binding of rac-Terazosin and Its Resolved Enantiomers

| Compound | Optical Purity | $a_1$ Receptor pK$_I$ (− log M) | $a_2$ Receptor pK$_I$ (− log M) | Selectivity Ratio* |
|---|---|---|---|---|
| S(−) | $[a]_D = -23.1°$ | 9.192 ± 0.112 | 7.036 ± 0.199 | 143 |
| R(+) | $[a]_D = +23.9°$ | 9.016 ± 0.083 | 5.938 ± 0.178 | 1197 |
| Racemic | | 9.192 ± 0.101 | 6.569 ± 0.129 | 420 |

*Antilog [pK$_I$($a_1$)-pK$_I$($a_2$)]

Examination of the data in Table 1 shows that the binding of the racemic compound and the two completely resolved enantiomers to the $a_1$ receptor is equivalent. On the other hand, there are significant differences in the binding of the racemic compound and the two completely resolved enantiomers at the $a_2$ receptor. This translates into a selectivity ratio for the dextrorotatory enantiomer more than eight-fold greater than that of the levorotatory enantiomer.

As discussed above, compounds which are active at $a_2$ receptors are implicated in controlling the release of norepinephrine and related catecholamines. Thus, it is believed that R(+)-2-[4-[(tetrahydro-2-furanyl)carbonyl]-1-piperazinyl]-6,7-dimethoxy-4-quinazolinamine possesses useful pharmaceutical properties while being less subject to undesirable side effects which flow from $a_2$-adrenergic binding activity.

The acute toxicities of the two enantiomeric forms of terazosin and the racemic compound were tested in adult male mice by intravenous administration, and the data appear in Table 2.

TABLE 2

| Compound | LD$_{50}$ mg/Kg | 95% Confidence Limits | Statistical Significance |
|---|---|---|---|
| R(+) | 306.6 | 265.8–445.1 | Racemic vs R(+) = $p < 0.05$ |
| S(−) | 204.6 | 178.8–234.1 | Racemic vs S(−) = $p < 0.05$ |
| Racemic | 247.9 | 230.5–273.0 | R(+) vs S(−) = $p < 0.05$ |

The data appearing in Table 2 show that R(+)-terazosin exhibits a 50% higher LD$_{50}$ (i.e. lower acute toxicity) than the corresponding S(−)-enantiomer.

The antihypertensive effects of R(+)-, S(−)-, and racemic terazosin were tested in several well-controlled experiments in the spontaneously hypertensive rat model. All three materials were dissolved in vehicle (0.2% methylcellulose) and administered orally at doses ranging from 0.1 to 10.0 mg/kg of body weight. As a control, the vehicle was administered orally. The compounds were administered in a volume of 2.0 ml/kg. All doses of the compound and vehicle were tested simultaneously in groups of eight to sixteen rats, randomly grouped.

The arterial and systolic blood pressure and heart rate were measured thirty minutes prior to and at intervals of 1, 5, 8, and 24 hours following administration of the test compounds. The data from these tests indicate that all three materials exhibited comparable dose-related antihypertensive effects in the spontaneously hypertensive rat model, although the R(+)-enantiomer consistently did not produce an increase in heart rate (tachycardia), whereas tachycardia was consistently observed with the S(−)-enantiomer or the racemic compound. While not holding to one theory to the exclusion of others, it is believed that the tachycardia associated with administration of the S(−)-enantiomer is due to the greater affinity of the S(−)-enantiomer for binding at the $\alpha_2$ adrenergic receptor and the lack of tachycardia associated with administration of the R(+)-enantiomer with its low affinity for the $\alpha_2$ receptors.

The effect upon $\alpha_2$-stimulated norepinephrine release of R(+)-terazosin and the S(−)-enantiomer and racemic compound were evaluated in the stimulated rat vas deferens model. Vas deferens tissue from male Wistar rats was cleaned of extraneous tissue and mounted between platinum stimulating electrodes and suspended in a tissue bath. The tissues were stimulated transmurally until the preparation stabilized, generally after about 60–80 minutes. After the twitch response became constant, a stimulus was applied at a frequency of 0.1 Hz for the duration of the dose-response study.

Clonidine was used as a control for inhibiting the twitch response, with 10 minute contact times at increasing doses until the stimulated response was attenuated to zero. The stimulus was then reduced to once every five minutes and the tissue washed until the twitch response was restored. After this, the 0.1 Hz signal was again applied and clonidine was administered together with test compound. All responses were calculated as percent reduction in the twitch response.

In this in vitro model, clonidine, a standard $\alpha_2$ adrenoreceptor agonists (i.e. stimulant) inhibits norepinephrine release from the adrenergic nerve endings and thus inhibits the contractile response of tissue. S(−)-Terazosin antagonized this clonidine-mediated effect and demonstrated competitive antagonism on the $\alpha_2$ adrenoceptor in this model. rac-Terazosin displayed less $\alpha_2$-adrenoreceptor inhibitory potency in this model, while the R(+)-enantiomer was devoid of $\alpha_2$-adrenoreceptor affinity and thus failed to affect $\alpha_2$-adrenoreceptor mediated norepinephrine release when tested up to the concentration of 3.0 $\mu$molar. The interaction of S(−)-terazosin with the $\alpha_2$-adrenoreceptor in this model was dose-dependent and exhibited pA$_2$ values of 5.83 and 5.95 in duplicate measurements at 1.0 $\mu$molar concentration and 5.8 and 5.99 in duplicate measurements at 3 $\mu$molar concentration. No pA$_2$ values could be measured for the R(+)-enantionmer. (The pA$_2$ values is the negative logarithm of the equilibrium dissociation constant for the antagonist-receptor complex, calculated from pharmacological functional data, and is a measure of the affinity of the antagonist at the particular receptor.)

The present invention also provides pharmaceutical compositions which comprise one or more of the compounds of formula I above formulated together with one or more non-toxic pharmaceutically acceptable carriers. The pharmaceutical compositions may be specially formulated for oral administration in solid or liquid form, for parenteral injection, or for rectal, vaginal, or topical administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intraveneous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like, Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsuled matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable nonirritating excipients or carriers such as cocoa butter; polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidly cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

For use as an antihypertensive agent, the compound of this invention is generally dosed orally at levels of about 0.01 mg to about 250 mg, more preferably of about 0.1 mg to about 100 mg of active compound per kilogram of body weight per day to a mammalian patient. If desired, the effective daily dose may be divided into multiple doses for purposes of administration, e.g. two to four separate doses per day.

EXAMPLE 1

Preparation of
R(+)-2-[4-[(tetrahydro-2-furanyl)carbonyl]-1-
piperazinyl]-6,7-dimethoxy-4-quinazolinamine Step 1—Preparation of R(+)-tetrahydrofuroic acid Using the procedure detailed in *Can. J. Chem.*, 61:1383-1386 (1983), racemic tetrahydro-2-furoic acid was first converted to a mixture of the diastereomeric brucine salts by reaction with (−)-brucine in ethyl acetate. The crude brucine salt of R(+)-tetrahydro-2-furoic acid which first precipitated had a melting point of 191°-197° C. and an optical rotation $[a]_D^{23} = -7.86°$ (C=1, methanol). The material was recrystallized three times from ethyl acetate to yield material melting at 200°-203° C. and having an optical rotation $[a]_D^{23°\ C.} = -4.8°$ (C=1, methanol) (literature $[a]_D = -5.8°$ (C=1, methanol)).

The salt was acidified to recover R(+)-tetrahydro-2-furoic acid, b.p. 57°-58° C. at 0.1 mm Hg, refractive index, $\eta_D^{25} = 1.4953$, optical rotation $[a]_D^{22°\ C.} = +33.37°$ (C=1, chloroform) (literature value $[a]_D = +30.4°$ (C=1, chloroform).

Step 2—Preparation of R(+)-2-[4-[(tetrahydro-2-furanyl)carbonyl]-1-piperazinyl]-6,7-dimethoxy-4-quinazolinamine R(+)-Tetrahydro-2-furoic acid was dissolved in tetrahydrofuran and 2.0 g (0.017 mole) dicyclohexylcarbodiimide was added followed by 3.50 g (0.017 mole) N-hydroxysuccinimide. The mixture was stirred overnight at room temperature. The precipitated dicyclohexylurea which formed was collected by filtration and the residue washed with a small amount of tetrahydrofuran. The solid was discarded and the washings added to the filtrate.

To the filtrate were added a solution of 4.91 g (0.017 mole) of 4-amino-6,7-dimethoxy-2-piperazinyl-4-quinazoline in tetrahydrofuran. The resulting mixture was stirred overnight at room temperature. The solid which had precipitated was collected by filtration and washed several times with tetrahydrofuran. The washings were combined with the filtrate with was evaporated to dryness. The residual solid was taken up in a 5/1 mixture of methylene chloride/methanol and the resulting mixture distilled to remove the methylene chloride. The removed methylene chloride was replaced by an equal volume of methanol, at which point the product began to crystallize from solution. The solution was allowed to cool to room temperature and stand for several hours, yielding R(+)-2-[4-[(tetrahydro-2-furanyl)carbonyl]-1-piperazinyl]-6,7-dimethoxy-4-quinazolinamine, m.p. 272°-274° C., optical rotation $[a]_D^{22°\ C.} = 34.83°$ (C=1, 3N hydrochloric acid). acid).

EXAMPLE 2

Preparation of
R(+)-2-[4-[(tetrahydro-2-furanyl)carbonyl]-1-
piperazinyl]-6,7-dimethoxy-4-quinozolinamine,
hydrochloride salt dihydrate The hydrochloride salt dihydrate was prepared by heating an ethanol solution of R(+)-2-[4-[(tetrahydro-2-furanyl)carbonyl]-1-piperazinyl]-6,7-dimethoxy-4-quinazolinamine to near reflux and adding slightly more than one equivalent of concentrated aqueous hydrochloric acid. Solution occurred immediately, and the solution was allowed to cool to room temperature and stand for several hours. The precipitated which formed was collected by filtration, washed with ethanol, and dried to yield R(+)-2-[4-[(tetrahydro-2-furanyl)carbonyl]-1-piperazinyl]-6,7-dimethoxy-4-quinazolinamine, hydrochloride salt dihydrate having a melting point of 260.5°-263.5° C. and an optical rotation $[a]_D^{28.5°\ C.} = 23.9°$ (C=1, water).

EXAMPLE 3

Preparation of
S(−)-2-[4-[(tetrahydro-2-furanyl)carbonyl]-1-
piperazinyl]-6,7-dimethoxy-4-quinazolinamine Step 1—Preparation of S(−)-tetrahydrofuroic acid Using the procedure detailed in *Can. J. Chem.*, 61:1383-1386 (1983), racemic tetrahydro-2-furoic acid was first converted to a mixture of the diastereomeric ephedrine salts by reaction with (+)-ephedrine in ethyl acetate. The crude S(−)-ephedrine salt which first precipitated had a melting point of 114°-117° C. The material was recrystallized four times from ethyl acetate to yield material melting at 115°-117° C. and having an optical rotation $[a]_D^{26.5°\ C.} = +13.4°$ (C=1, methanol) (literature $[a]_{D-} +13.8°$).

The salt was acidified to recover the S(−)-tetrahydro-2-furoic acid, b.p. 60° C. at 0.5 mm Hg, refractive index, $h_D^{25} = 1.4582$, optical rotation $[a]_D^{22°} = -32.02°$ (C=1, chloroform) (literature $[a]_D = -30.1°$ (C=1, chloroform)).

Step 2—Preparation of S(−)-2-[4-[(tetrahydro-2-furanyl)carbonyl]-1-piperazinyl]-6,7-dimethoxy-4-quinazolinamine The procedure employed was the same as that described above in Example 1 for the R(+)-enantiomer, yielding S(−)-2-[4-[(tetrahydro-2-furanyl)carbonyl]-1-piperazinyl]-6,7-dimethoxy-4-quinazolinamine, m.p. 269.5°-271.1° C., optical rotation $[a]_D^{22°\ C.} = -26.9°$ (C=1, 3N hydrochloric acid).

EXAMPLE 4

Preparation of
S(−)-2-[4-[(tetrahydro-2-furanyl)carbonyl]-1-
piperazinyl]-6,7-dimethoxy-4-quinazolinamine,
hydrochloride salt The procedure employed was the same as in Example 2 for the preparation of the hydrochloride salt of the R(+)-enantiomer. M.p. 271.5°-273° C. (dec.), optical rotation $[a]_D^{28.5°\ C.} = -23.1°$ (C=1, water).

While there have been described and illustrated what are believed to be the preferred embodiments of the present invention, it will be obvious to one of ordinary skill in the art that various modifications thereof can be made without departing from the scope of the invention as it is defined by the appended claims.

We claim:

1. The compound having the name R(+)-2-(4-((tetrahydro-2-furanyl)carbonyl)piperazinyl)-6,7-dimethoxy-4-quinazolinamine hydrochloride dihydrate having an optical rotation $[\alpha]_D^{28.5°\ C.}$ (C=1, water) of 23.9° or greater.

2. A pharmaceutical composition comprising a therapeutically effective amount of the compound as defined by claim 1 in combination with a pharmaceutically acceptable carrier.

3. A method of treating hypertension in a mammal in need of such treatment comprising administering a therapeutically effective amount of of the compound as defined by claim 1.

4. A method of treating benign prostatic hyperplasia in a mammal in need of such treatment comprising administering a therapeutically effective amount of the compound as defined by claim 1.

5. A method of treating hyperinsulinemia in a mammal in need of such treatment comprising administering a therapeutically effective amount of the compound as defined by claim 1.

6. A method of treating congestive heart failure in a mammal in need of such treatment comprising administering a therapeutically effective amount of the compound as defined by claim 1.

* * * * *

UNITED STATES PATENT AND TRADEMARK OFFICE
CERTIFICATE OF CORRECTION

PATENT NO. : 5,212,176

DATED : May 18, 1993

INVENTOR(S) : John J. Kynel, Lake Forest; Bruce W. Horrom, Waukegan, both of Ill.

It is certified that error appears in the above-identified patent and that said Letters Patent is hereby corrected as shown below:

Column 10, Line 67, Delete the second ---of---

Signed and Sealed this

Twelfth Day of April, 1994

*Attest:*

BRUCE LEHMAN

*Attesting Officer*   Commissioner of Patents and Trademarks